United States Patent
Thompson et al.

(10) Patent No.: US 9,155,599 B2
(45) Date of Patent: Oct. 13, 2015

(54) SYSTEMS AND PROCESSES FOR FORMING ANATOMICAL FEATURES IN DENTURES

(75) Inventors: Timothy C. Thompson, Fountain Hills, AZ (US); Scott C. Keating, Louisville, CO (US); Andrzej J. Jakson, Amherst, NY (US)

(73) Assignee: Global Dental Science LLC, Scottsdale, AZ (US)

( * ) Notice: Subject to any disclaimer, the term of this patent is extended or adjusted under 35 U.S.C. 154(b) by 0 days.

(21) Appl. No.: 13/823,621

(22) PCT Filed: Nov. 3, 2011

(86) PCT No.: PCT/US2011/059230
§ 371 (c)(1),
(2), (4) Date: Mar. 14, 2013

(87) PCT Pub. No.: WO2012/061652
PCT Pub. Date: May 10, 2012

(65) Prior Publication Data
US 2013/0216978 A1    Aug. 22, 2013

Related U.S. Application Data

(63) Continuation-in-part of application No. 12/939,138, filed on Nov. 3, 2010.

(51) Int. Cl.
*A61C 13/00*    (2006.01)
*A61C 13/01*    (2006.01)
(Continued)

(52) U.S. Cl.
CPC ............... *A61C 13/01* (2013.01); *A61C 9/0006* (2013.01); *A61C 13/0004* (2013.01); *A61C 13/10* (2013.01); *A61C 13/34* (2013.01); *A61C 9/004* (2013.01); *Y10T 29/49567* (2015.01)

(58) Field of Classification Search
CPC ........ A61C 8/00; A61C 9/004; A61C 9/0046; A61C 13/0001; A61C 13/0004; A61C 13/0006; A61C 13/0009; A61C 13/0024; A61C 13/0027; A61C 13/01; A61C 13/08; A61C 13/10; A61C 13/1003; A61C 13/1013; A61C 13/34
USPC .............. 433/167, 168.1, 171, 172, 191, 192, 433/199.1, 200.1, 202.1, 213, 214, 215
See application file for complete search history.

(56) References Cited

U.S. PATENT DOCUMENTS

| 200,445 A | 2/1878 | Fahnestock |
| 321,847 A | 7/1885 | Peirce et al. |

(Continued)

FOREIGN PATENT DOCUMENTS

| JP | 2008307281 | 12/2008 |
| WO | 2001032096 | 12/2001 |

(Continued)

OTHER PUBLICATIONS

USPTO; Final Office Action dated Mar. 6, 2014 in U.S. Appl. No. 13/249,210.

(Continued)

*Primary Examiner* — Yogesh Patel
(74) *Attorney, Agent, or Firm* — Snell & Wilmer L.L.P.

(57) ABSTRACT

The system of a preferred embodiment uses a process whereby a true replication of the patient's jaw structure is created in a digital three dimensional model. This true replication is then used to precisely locate and/or copy the anatomical landmarks of the patient for use in fabricating a denture base for use in a denture for the individual patient. This system is able to create a denture with precisely located features corresponding to the anatomical landmarks of the patient with little manual intervention.

18 Claims, 11 Drawing Sheets

(51) Int. Cl.
*A61C 13/10* (2006.01)
*A61C 9/00* (2006.01)
*A61C 13/34* (2006.01)

(56) References Cited

U.S. PATENT DOCUMENTS

| | | |
|---|---|---|
| 711,324 A | 10/1902 | Lacy |
| 1,223,450 A | 4/1917 | Van Allen |
| 1,293,627 A | 2/1919 | Bowers |
| 1,585,348 A | 5/1926 | Hick et al. |
| 1,652,910 A | 12/1927 | Psayla |
| 1,714,185 A | 5/1929 | Hugh |
| 1,863,591 A | 6/1932 | Crowell |
| 1,914,606 A | 6/1933 | Kinna et al. |
| 2,107,181 A * | 2/1938 | Guyton ............... 433/199.1 |
| 2,418,833 A | 4/1947 | Harris et al. |
| 2,472,492 A | 6/1949 | Saffir |
| 2,641,835 A | 6/1953 | Greenmun |
| 2,985,961 A | 5/1961 | Schwartz |
| 2,994,957 A | 8/1961 | Mcleod |
| 3,083,459 A | 4/1963 | McMurry et al. |
| 3,241,238 A | 3/1966 | Kertsten |
| 3,644,996 A | 2/1972 | Weinkle |
| 3,667,123 A | 6/1972 | Huey |
| 3,727,309 A | 4/1973 | Huey |
| 3,748,739 A | 7/1973 | Thibert |
| 3,813,777 A | 6/1974 | Van Handel et al. |
| 4,029,632 A | 6/1977 | Gross et al. |
| 4,227,877 A | 10/1980 | Tureaud et al. |
| 4,247,287 A | 1/1981 | Gigante |
| 4,299,573 A | 11/1981 | Ricci |
| 4,533,325 A | 8/1985 | Blair |
| 4,591,341 A | 5/1986 | Andrews |
| 4,634,377 A | 1/1987 | Behrend |
| 4,784,608 A | 11/1988 | Mays |
| 4,931,016 A | 6/1990 | Sillard |
| 5,098,296 A | 3/1992 | Cullen |
| 5,151,044 A | 9/1992 | Rotsaert |
| 5,188,529 A | 2/1993 | Luth |
| 5,427,906 A | 6/1995 | Hansen |
| 5,672,305 A | 9/1997 | Kogure |
| 5,711,668 A * | 1/1998 | Huestis ............... 433/167 |
| 5,716,214 A | 2/1998 | Lund |
| 5,718,584 A | 2/1998 | Wong |
| 5,833,461 A * | 11/1998 | Wong ............... 433/168.1 |
| 5,839,900 A | 11/1998 | Billet et al. |
| 6,056,547 A | 5/2000 | Names |
| 6,139,322 A | 10/2000 | Liu |
| 6,149,427 A * | 11/2000 | Van Handel ............... 433/37 |
| 6,224,372 B1 | 5/2001 | Ibsen et al. |
| 6,227,851 B1 | 5/2001 | Chishti |
| 6,384,107 B2 | 5/2002 | Liu |
| 6,422,864 B1 | 7/2002 | Glatt |
| 6,488,503 B1 | 12/2002 | Lichkus et al. |
| 6,616,444 B2 | 9/2003 | Andreiko et al. |
| 6,851,949 B1 | 2/2005 | Sachdeva |
| 7,021,934 B2 | 4/2006 | Aravena |
| 7,153,135 B1 | 12/2006 | Thomas |
| 7,234,940 B2 | 6/2007 | Weissman |
| 7,433,810 B2 | 10/2008 | Pavloskaia et al. |
| 7,474,932 B2 * | 1/2009 | Geng ............... 700/98 |
| 7,758,345 B1 | 7/2010 | Christensen |
| 8,043,091 B2 | 10/2011 | Schmitt |
| 8,348,669 B1 | 1/2013 | Schmitt |
| 8,567,408 B2 | 10/2013 | Roettger |
| 8,641,938 B2 | 2/2014 | Howe |
| 8,801,431 B2 | 8/2014 | Thompson |
| 8,875,398 B2 | 11/2014 | Balshi et al. |
| 9,055,993 B2 | 6/2015 | Grobbee et al. |
| 2002/0180760 A1 | 12/2002 | Rubbert et al. |
| 2003/0108845 A1 | 6/2003 | Giovannone |
| 2003/0162147 A1 | 8/2003 | Dequeker |
| 2003/0211444 A1 | 11/2003 | Andrews |
| 2004/0005530 A1 | 1/2004 | Mullaly |
| 2004/0219490 A1 | 11/2004 | Gartner et al. |
| 2005/0175957 A1 | 8/2005 | Haje |
| 2005/0186539 A1 | 8/2005 | McLean et al. |
| 2005/0284489 A1 | 12/2005 | Ambis |
| 2006/0040232 A1 | 2/2006 | Shoup |
| 2006/0040236 A1 | 2/2006 | Schmitt |
| 2006/0210945 A1 | 9/2006 | Savic et al. |
| 2006/0286507 A1 | 12/2006 | Dequeker |
| 2007/0231774 A1 | 10/2007 | Massad |
| 2008/0085489 A1 | 4/2008 | Schmitt |
| 2008/0090207 A1 | 4/2008 | Rubbert |
| 2008/0127698 A1 | 6/2008 | Luckey et al. |
| 2008/0206710 A1 | 8/2008 | Kruth et al. |
| 2008/0206714 A1 * | 8/2008 | Schmitt ............... 433/215 |
| 2008/0209974 A1 | 9/2008 | Ewolski et al. |
| 2008/0300716 A1 * | 12/2008 | Kopelman et al. ............ 700/182 |
| 2009/0148813 A1 | 6/2009 | Sun et al. |
| 2009/0287332 A1 | 11/2009 | Adusumilli et al. |
| 2009/0291407 A1 | 11/2009 | Kuo |
| 2009/0325125 A1 | 12/2009 | Diangelo et al. |
| 2010/0015572 A1 | 1/2010 | Dirkes et al. |
| 2010/0062394 A1 | 3/2010 | Jones et al. |
| 2010/0086186 A1 | 4/2010 | Zug et al. |
| 2010/0094446 A1 | 4/2010 | Baloch et al. |
| 2010/0324875 A1 | 12/2010 | Kalili |
| 2011/0045442 A1 | 2/2011 | Adusumilli |
| 2011/0112804 A1 | 5/2011 | Chishti et al. |
| 2011/0129796 A1 | 6/2011 | Riggio |
| 2011/0236856 A1 | 9/2011 | Kanazawa et al. |
| 2011/0244417 A1 | 10/2011 | Hilsen et al. |
| 2012/0058449 A1 | 3/2012 | Sklarski et al. |
| 2012/0178045 A1 | 7/2012 | Massad |
| 2012/0179281 A1 | 7/2012 | Steingart et al. |
| 2012/0258426 A1 | 10/2012 | Boe |
| 2012/0285019 A1 | 11/2012 | Schechner et al. |
| 2012/0329008 A1 | 12/2012 | Fishman et al. |
| 2013/0108988 A1 | 5/2013 | Simoncic |
| 2013/0209962 A1 | 8/2013 | Thompson et al. |
| 2013/0218532 A1 | 8/2013 | Thompson et al. |
| 2013/0249132 A1 | 9/2013 | Thompson et al. |
| 2013/0280672 A1 | 10/2013 | Thompson et al. |
| 2013/0316302 A1 | 11/2013 | Fisker |
| 2014/0045967 A1 | 2/2014 | Thomas et al. |
| 2014/0272796 A1 | 9/2014 | Grobbee et al. |
| 2015/0010885 A1 | 1/2015 | Balshi et al. |
| 2015/0037760 A1 | 2/2015 | Thompson et al. |
| 2015/0064653 A1 | 3/2015 | Grobbee et al. |
| 2015/0134094 A1 | 5/2015 | Thompson et al. |

FOREIGN PATENT DOCUMENTS

| | | | |
|---|---|---|---|
| WO | 2009105661 | 8/2009 | |
| WO | WO 2009105700 A2 * | 8/2009 | ............ A61C 13/00 |
| WO | 2010022479 | 3/2010 | |
| WO | 2012041329 | 4/2012 | |
| WO | 2012061652 | 5/2012 | |
| WO | 2012061655 | 5/2012 | |
| WO | 2012061659 | 5/2012 | |
| WO | 2012061660 | 5/2012 | |
| WO | 2014130536 | 8/2014 | |
| WO | 2015031062 | 3/2015 | |

OTHER PUBLICATIONS

USPTO; Restriction Requirement dated Dec. 23, 2013 in U.S. Appl. No. 13/823,466.

EPO; European Search Report dated Mar. 4, 2014 in Application No. 11838839.6.

USPTO; Notice of Allowance dated Jun. 6, 2014 in U.S. Appl. No. 13/249,210.

USPTO; Non-Final Office Action dated Jun. 6, 2014 in U.S. Appl. No. 13/823,466.

USPTO; Non-Final Office Action dated Jun. 20, 2014 in U.S. Appl. No. 13/830,963.

USPTO; Restriction Requirement dated Jul. 2, 2014 in U.S. Appl. No. 14/195,348.

EPO; European Search Report and Opinion dated Mar. 3, 2014 in Application No. 11838843.8.

(56) References Cited

OTHER PUBLICATIONS

PCT; International Search Report and Written Opinion dated Jul. 25, 2014 in Application No. PCT/US2014/017136.
USPTO; Office Action dated Sep. 24, 2013 in U.S. Appl. No. 13/249,210.
USPTO; Final Office Action dated dated Nov. 7, 2014 in U.S. Appl. No. 13/830,963.
USPTO; Office Action dated Jan. 5, 2015 in U.S. Appl. No. 12/939,136.
USPTO; Restriction Requirement dated Feb. 12, 2015 in U.S. Appl. No. 13/369,238.
USPTO; Advisory Action dated Feb. 23, 2015 in U.S. Appl. No. 13/830,963.
USPTO; Non-Final Office Action dated Dec. 19, 2014 in U.S. Appl. No. 14/013,295.
PCT; International Search Report and Written Opinion dated Jul. 18, 2012 in Application No. PCT/US2011/059230.
PCT; International Preliminary Report on Patentability dated May 8, 2013 in Application No. PCT/US2011/059230.
PCT; International Search Report and Written Opinion dated Jul. 18, 2012 in Application No. PCT/US2011/059235.
PCT; International Preliminary Report on Patentability dated May 8, 2013 in Application No. PCT/US2011/059235.
PCT; International Search Report and Written Opinion dated Jul. 9, 2012 in Application No. PCT/US2011/059239.
PCT; International Preliminary Report on Patentability dated May 8, 2013 in Application No. PCT/US2011/059239.
PCT; International Search Report and Written Opinion dated Jul. 18, 2012 in Application No. PCT/US2011/059240.
PCT; International Preliminary Report on Patentability dated May 8, 2013 in Application No. PCT/US2011/059240.
USPTO; Restriction Requirement dated Sep. 5, 2014 in U.S. Appl. No. 13/823,621.
USPTO; Office Action dated Aug. 21, 2014 in U.S. Appl. No. 14/195,348.
USPTO; Final Office Action dated Oct. 21, 2014 in U.S. Appl. No. 14/195,348.
PCT; International Search Report and Written Opinion dated Aug. 7, 2014 in Application No. PCT/US2014/023654.
USPTO; Non-Final Office Action dated Apr. 9, 2015 in U.S. Appl. No. 12/939,138.
USPTO; Final Office Action dated Mar. 26, 2015 in U.S. Appl. No. 13/823,466.
USPTO; Notice of Allowance dated Apr. 13, 2015 in U.S. Appl. No. 14/013,295.

* cited by examiner

SYSTEMS AND PROCESSES FOR FORMING ANATOMICAL FEATURES IN DENTURES

CROSS-REFERENCE TO RELATED APPLICATIONS

This application is a Continuation-In-Part of, claims priority to and the benefit of, U.S. patent application Ser. No. 12/939,138 filed Nov. 3, 2010, and entitled "SYSTEMS AND PROCESS FOR FORMING ANATOMICAL FEATURES IN DENTURES" and PCT Application Serial No. PCT/US11/59230 filed Nov. 3, 2011, and entitled "SYSTEMS AND PROCESS FOR FORMING ANATOMICAL FEATURES IN DENTURES". Each aforementioned application is incorporated by reference in its entirety for all purposes.

FIELD OF THE INVENTION

This invention relates to the field of manufacturing of dentures and particularly forming anatomical and functional features in dentures.

BACKGROUND

Dentures need to be closely fitted to anatomical landmarks on the patient in order for the denture to comfortably fit as well as to be under the neuromuscular control of the patient. It is critical for the dentures to properly fit in order for the dentures to be worn comfortably and securely without the embarrassment of falling out during use.

The anatomical landmarks are typically located relative to the patient's anatomy by using a customized denture impression tray. Thermoplastic molding compound is applied along the peripheral edges of the tray which is positioned in the patient while the compound is soft. The patient manipulates their jaw while the compound is setting to provide in the impression appropriate clearances within the buccal, labial and/or lingual folds. This process is uncomfortable for the patient and does not provide precise location of the anatomical features. The resulting impressions are typically used in creating a wax rim. The wax rim is tried in the patient and marked to provide areas which need to be carved for a better fit. This requires skill on the part of the dentist and technicians.

One critical area of fit for the denture is the post dam. The post dam on a denture is a ridge along the back of the denture which presses slightly into the posterior palate to form a seal. The increased thickness of the denture along a narrow border adds pressure on the tissue and maintains a vacuum seal. Without this sealing effect, the upper denture the vacuum between the denture and the roof of the mouth is reduced or lost and the denture loosens as the wearer talks, chews or swallows. This seal is critical for the upper denture to be secure in the patient.

The ideal location for the post dam is along the junction of the hard and soft palates. The junction between the hard and soft palate where the denture border lies is neither a straight line nor of uniform consistency. It is harder in the midline and soft on both sides of the midline. Thus, an ideal post dam has to reflect the anatomy and features of that palate of the mouth. If the denture extends too far to the rear of the mouth, the patient may suffer from gagging. If the denture extends too much into the hard palate, the denture will likely lose the vacuum seal and will not fit Currently, the post dam is created on the denture by modifying the impressions or by application of a wax material to the area of the plaster model representing the roof of the mouth. Both require the use of a plaster model of the denture upon which the post dam is carved by a technician based on the estimation of where the line between the hard and soft palate occurs in the impression into the mold from the denture will be fabricated. Both techniques are less than precise in locating the ideal position. Thus the precision on where the post dam is located depends upon the quality of the impressions and the skill of the technician.

Another set of anatomical feature that are critical for the proper use of dentures are the labial and buccal frenae. The labial frenum attaches to the center of the upper lip and between the upper two front teeth while the buccal frenums attach the alveolar ridge to the cheek on each side of the mouth. If the matching notches of the denture are not located precisely for the labial frenum and the buccal frenums, the denture can often be pulled loose. Currently these frenums are visually located by the dentist or technician and the notches formed by a file in the impressions.

The rugae is typically neglected in the creation of dentures. The palatial rugae is asymmetrical and has irregular elevations of the mucosa located in the anterior third of the palate. Each individual has a unique rugae which can affect the speech of the individual. Currently, most dentures do not include a rugae and are smooth, instead. In those instances where a denture does include a rugae, the rugae is typically formed from a template rather than having a unique rugae for each patient.

Thus, presently there is no process for creating dentures that have the precise fit to or mimicking of the anatomical features of the patients mouth.

SUMMARY OF THE INVENTION

The present invention provides systems and processes for creating dentures that have features precisely located and formed to provide a close comfortable fit for the dentures in the patient. These features provide critical functional and aesthetic improvement for the fit and comfort of the patient. The system of a preferred embodiment uses a process whereby a true replication of the patient's jaw structure is created in a digital three dimensional model. This true replication is then used to precisely locate and/or copy the anatomical landmarks of the patient for use in fabricating a denture base for use in a denture for the individual patient.

The term denture base generally refers to the part of a denture that fits the oral mucosa of the basal seat, restores the normal contours of the soft tissues of the edentulous mouth, and supports the artificial teeth. The term denture refers to the denture base with the artificial teeth attached. The term anatomical landmarks refers to the structures on the anatomy of the wearer that define the periphery of the denture. The term anatomical features includes the features corresponding to the anatomical landmarks of the wearer as well as aesthetic and functional features that are created in the denture.

One anatomical landmark that is determined preferably by the system, but alternatively by a technician using the system is the line between the hard and soft palates. This line is irregular and difficult to determine precisely using current techniques. One preferred embodiment of the present invention determines this line from the digital model. Once this line is determined, a post dam is created on the digital model.

Another set of anatomical landmarks that are determined are the labial frenum and the buccal frenums. The precise location of the frenums in a preferred embodiment is identified so that notches matching these frenums are precisely located and shaped in the denture base. This minimizes dislocation of the denture during speech and improves the comfort, fit and aesthetics of the denture.

Another preferred embodiment accentuates the buccal reflection of the patient. This accentuation is called the buccal roll. The buccal roll for purposes of this patent is defined as the small rounded ridge that is added to the denture to improve vacuum adherence, goes from the anterior middle back to the most posterior points on the outer margin. From this precise location of the buccal roll, a slight undercut can be formed in the denture base. The tissues and muscles surrounding the buccal roll will engage into the undercut to form a gripping region to further secure the denture.

The system of a preferred embodiment is able to precisely locate the margin, or trim line along the buccal reflection. This reduces the time for technician to carve or trim the denture base after molding and improves the comfort. This line can also be registered by the system to be included into the digital denture model and on the denture base.

Another embodiment of the present invention determines the soft tissue lines from the digital model so that they can be registered and included into the denture base for fabrication. In particular, the gingival margin where the gum ends on the teeth and the soft tissue surrounding the roots of the teeth below the gum are mimicked on the denture base. These soft tissue lines are largely for aesthetic reasons but also may improve the comfort to the patient.

One unique feature of a preferred embodiment is able to create the rugae of the individual patient for use in the denture base. The rugae is copied on the tissue side and mimicked on the teeth side. The rugae can also be accentuated or diminished as needed to improve the speech or comfort of the patient. Each rugae is unique to an individual and affect the speech and comfort of the individual. The rugae is also used to identify individuals for forensic purposes. The rugae is registered by the system for copying into the digital denture base model for selection or fabrication in the denture base.

The system of a preferred embodiment may also be used to select areas of the denture base that may be selectively thinned or thickened. This thinning or thickening may be done across the arch of the denture base, along the palatial region of the denture base or around the teeth pockets. The system or a user of the system is able to identify areas on the digital model that may be able to be thinner without jeopardizing structural integrity. The system can perform finite element analysis or other design on the fly techniques to determine the optimum design for the denture base and the denture teeth.

In a preferred embodiment, once the anatomical (including aesthetic and functional features) have been formed in the digital denture model, the denture teeth are selected or fabricated, the denture base is fabricated. The teeth are temporarily installed in the denture base to create a try-in denture. The try-in denture is then shipped to the dentist for a patient try-in. If the fit is not satisfactory, then the denture is used as a secondary impression tray and new impressions are created and scanned. These scans along with any additional changes in measurement data are put back into the system to render an improved digital denture model. New denture teeth are selected or fabricated based on this improved model, if necessary. The teeth are once again temporarily installed and the improved try-in denture is ready for another try-in with the patient.

The system of a preferred embodiment may also be to select and design areas where implant supports may be placed. These implant supports could be for example a bar or a housing. The placement could be a optimization process between the anatomical landmarks captured by a CT scan (bone density and shape) and the aesthetics and functional aspects of the denture.

This process is continued until the patient and dentist are satisfied with the denture. Once the denture has been deemed satisfactory, the denture is shipped back to the lab so that the teeth can be permanently installed and the final finish and polish procedures are performed. The finished denture is then shipped to the dentist for the patient final insert and acceptance.

These and other features of the claimed inventions will be evident from the ensuing detailed description of preferred embodiments, from the drawings and from the claims.

DETAILED DESCRIPTION

The present invention provides systems and process for the fabrication of dentures that correspond to anatomical landmarks of the patient. Descriptive embodiments are provided before for explanatory purposes. It is to be expressly understood that the present invention is not be limited to these descriptive embodiments. Other embodiments are considered to be within the scope of the present invention, including without limitation the use of the present invention for other applications, such as denture duplication, dental implants, and other dental and orthodontic applications. The descriptions below discuss the systems of the present invention as used in dental labs, but it is to be expressly understood that these systems could also be implemented in the dentist office or through a network allowing interaction between the dentist and the dental lab through the systems. The processes and systems of the present invention may also be used in combination with all or parts of the following applications, entitled System and Processes for Optimization for Dentures, Ser. No. 12/939,141; System and Process for Duplication of Dentures, Ser. No. 12/939,136; Combination Tool for Anatomical Measurement for Denture Manufacture, Ser. No. 13/249,210; and Removable Handle for Use with Dentures, Ser. No. 12/939,143; all of which are hereby incorporated herein by reference.

Overview

The terms denture base generally refers to the part of a denture that fits the oral mucosa of the basal seat, restores the normal contours of the soft tissues of the dentulous mouth, and supports the artificial teeth. The term denture refers to the denture base with the artificial teeth attached. The term anatomical landmarks refers to the structures on the anatomy of the wearer that define the periphery of the denture. The term anatomical features includes the features corresponding to the anatomical landmarks of the wearer as well as functional and aesthetic features that are created in the denture.

The system of a preferred embodiment uses a process whereby a true replication of the patient's jaw structure is created in a digital three dimensional model. This true replication is then used to precisely locate and/or copy the anatomical landmarks of the patient for use in fabricating a denture base for use in a denture for the individual patient.

Figure 1:
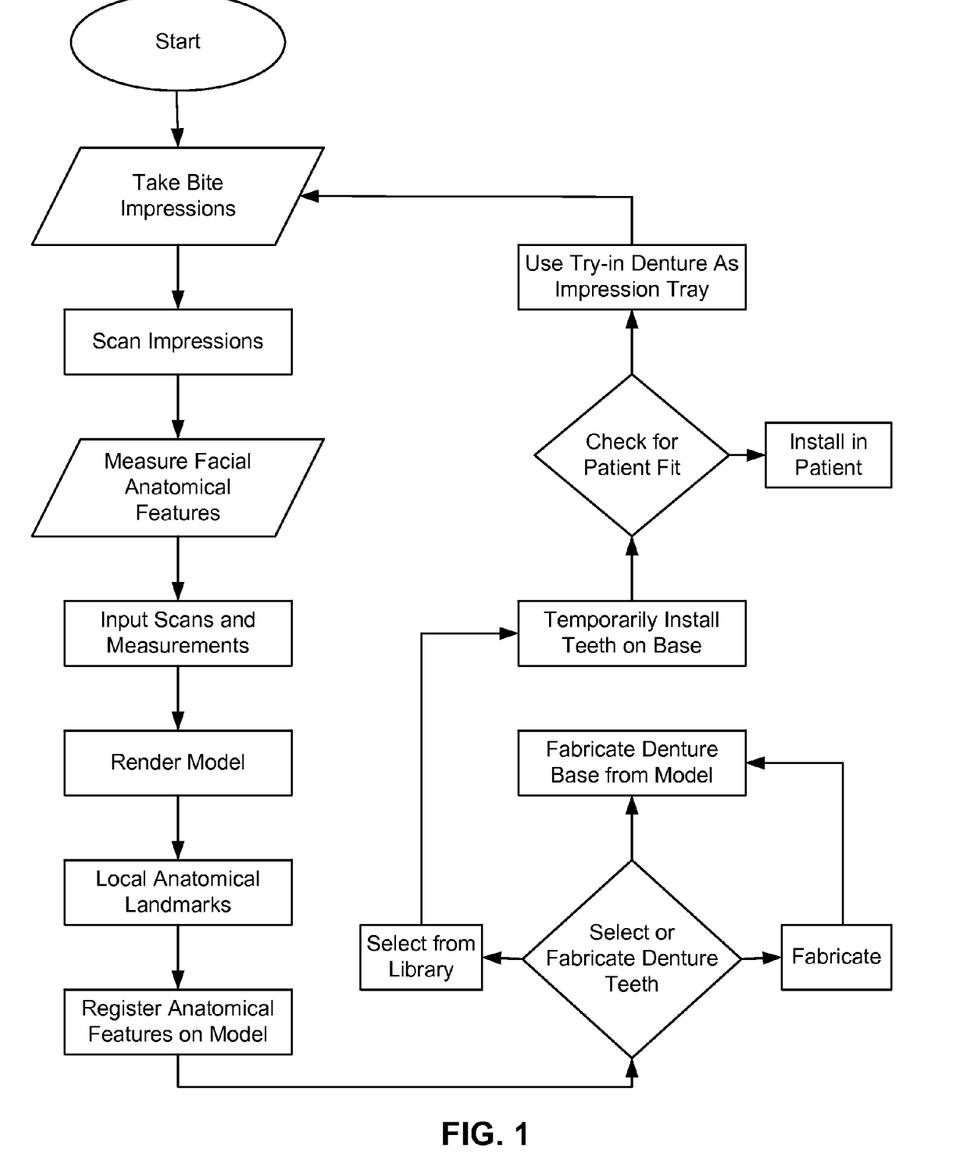
FIG. 1 illustrates a workflow diagram of an embodiment of the present invention.

In one preferred embodiment as described in the flow chart of FIG. 1, scans of the patient's bite impressions are taken and a number of measurements from the patient on their initial visit. These measurements are based on the anatomical features of the patient. The dentist may also provide information regarding to the selection of the teeth. This information is transmitted to the dental lab where the system creates a digital three dimensional model of the patient's jaw structure from the scans and from the measurements. It is to be expressly understood that other methods of creating a digital three dimensional model of the jaw structure may be used as well. The process described herein is only one embodiment for doing so.

Once the digital model has been created, denture teeth are selected from a library or fabricated directly for that digital model. This can be based on using a library and selecting the best denture teeth, through an optimization process as described in the above identified co pending application, or through another process.

The system of a preferred embodiment of the present invention either creates a digital denture base or modifies an existing digital denture base to create the best fit in the patient by precise use of the anatomical landmarks of the patient. These include locating the ideal location of the post dam, locating and forming the notches for the labial and buccal frenums, creating the idealized margins along the buccal reflection, creating the idealized gum line and root structures, creating a true copy of the patient's palatial rugae and duplicating that structure on the denture base, locating the soft tissue lines of the patients mouth, locating areas for dental implant structures and any other features that are useful or desirable from either a functional or aesthetic standpoint.

A description of one process and system for preforming the claimed inventions is described below. In this preferred embodiment, a digital three dimensional model of the patient's mouth and jaw structure is created from scanned bite impressions and from precise measurements of the anatomical features of the patient.

Measurement Process

Figure 2:
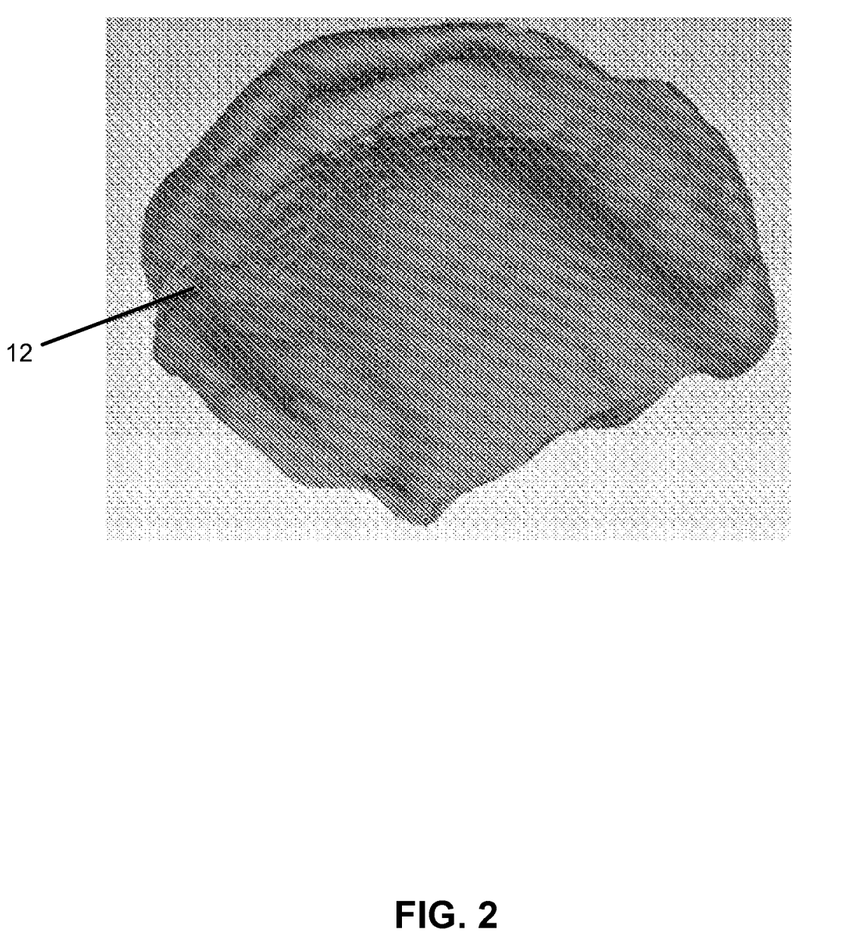
FIG. 2 is an inner and outer scan of a bite impression.

The dentist obtains data regarding several anatomical landmarks of the patient to send to the dental lab. First, the dentist takes the bite impressions. This can be done by using an upper bite impression tray, a lower bite impression tray and a centric relationship tray or a triple bite impression tray that simultaneously takes upper and lower and centric bite impressions. The resulting bite impressions are digitally scanned as shown in FIG. 2 and transmitted to the lab or directly into the system. The bite impressions provide the bite registration, the prepared area and the opposing teeth. Alternatively, or in conjunction with this process, an intraoral digital scanning may be done.

The dentist also takes additional measurements of anatomical features of the patient. These include, without limitation, the vertical height relation to the upper and lower bite alignment; the lip support of the patient; the smile line of the patient; the centric relationship of the patient; and the midline measurement. Other measurements may be taken as well.

The lip line measurement is intended to provide a measurement of the upper lip from the anterior papilla at rest. This is traditionally measured by a papillameter which consist of a vestibule shield, incisive papilla rest and an vertical handle with measurement increments.

The smile line measurement can also be determined by the papillameter. The device is inserted into position and the patient is requested to smile so that the lip line at that position from the anterior papilla can be measured.

The midline is determined from typically from the existing intraoral anatomic structures, usually the maxillary anterior labial frenum.

The vertical height dimension is typically determined from measurements taken from nose and chin reference points. Measurements of the vertical height are taken at rest and of the vertical dimension of occlusion.

A centric tray is commonly used to take a double arch registration to record vertical and centric jaw registration.

The occlusal plane is an orientation of the position of an imaginary occlusal plane which theoretically touches the incisal edges of the incisors and tips of the occluding surface of the posterior teeth. A normal occlusal plane extends parallel to a line drawn from the tragus of the ear to the ala of the nose and parallel to the interpupillary line (Kamper's Line). This ensures that the patient will not dislodge the lower denture, particularly while eating and not bite the lateral borders of the tongue. Tools for measuring the occlusal plane typically include a thin flat plane have a curved bite piece and a pair of laterally and distally extending wings projecting from the bite piece.

There are individual tools for each of these measurements. A single tool for obtaining all of these measurements is disclosed in application Ser. No. 13/249,210 entitled Combination Tool for Anatomical Measurement for Denture Manufacture, and is incorporated by reference herein above. In a preferred embodiment of the present invention, this tool is used to supply the necessary measurements for the optimization process for designing a denture mold.

The dentist also selects the teeth to be fitted into the denture base. Typically, the dentist will use a facial meter, anterior tooth selection guide and a library catalog to determine the appropriate teeth. Other methods may be used as well along with the determination of the appropriate shading of the teeth.

Figure 3:
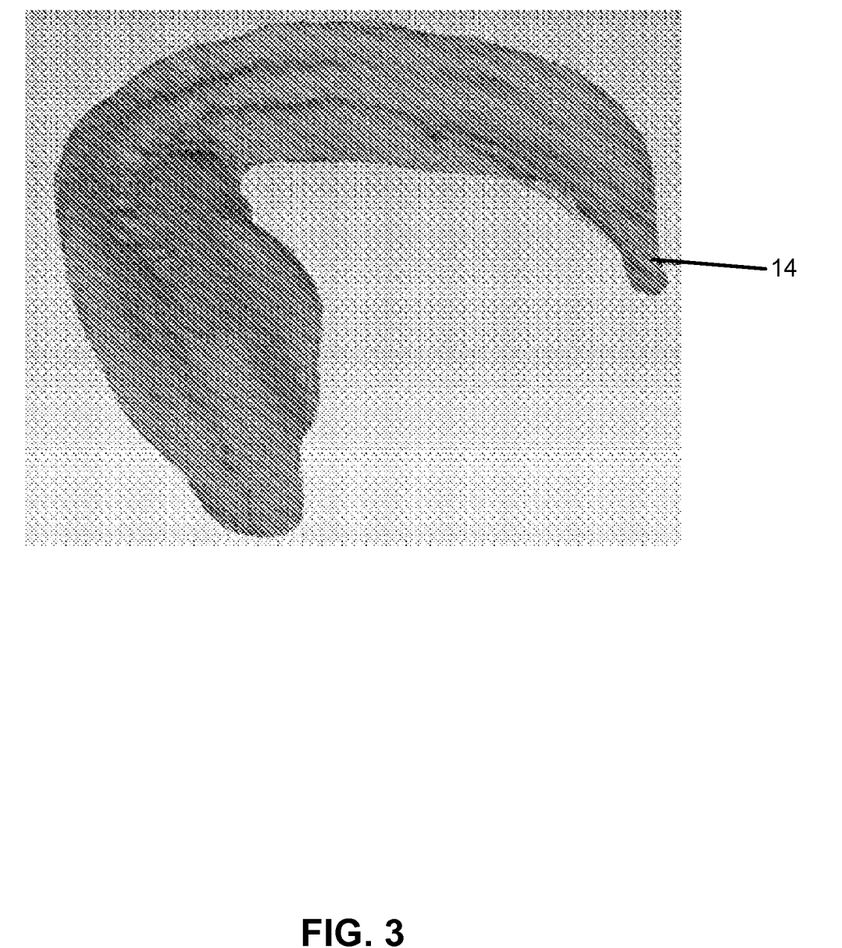
FIG. 3 is a rendition of a three dimensional model of a denture base.

The scan, measurements and teeth selection are then transmitted to the dental lab or directly into the system System The scanned images 12, 14 of the bite impressions and the measurements are then transmitted into a system that will process this information to create the digital three dimensional model. Systems for creating such digital three dimensional models are disclosed in U.S. Pat. No. 6,616,444, assigned to Ormco Corporation and patents relating to that patent, U.S. Pat. No. 6,851,949, assigned to OraMetrix, Inc. and patents relating to that patent; and U.S. Pat. No. 7,433,810, assigned to Align Technology, Inc. and patents relating to that patent, all of the above cited patents and patents and published patent applications relating to them are incorporated herein by reference. These systems are disclosed for use with orthodontic appliances. The present invention takes the information from these systems and utilizes the additional information described above in regard to the measurements of the patient's anatomy and impressions to create a digital model 20 as shown in FIG. 3 for use with creating and optimizing a denture base.

Figure 4:
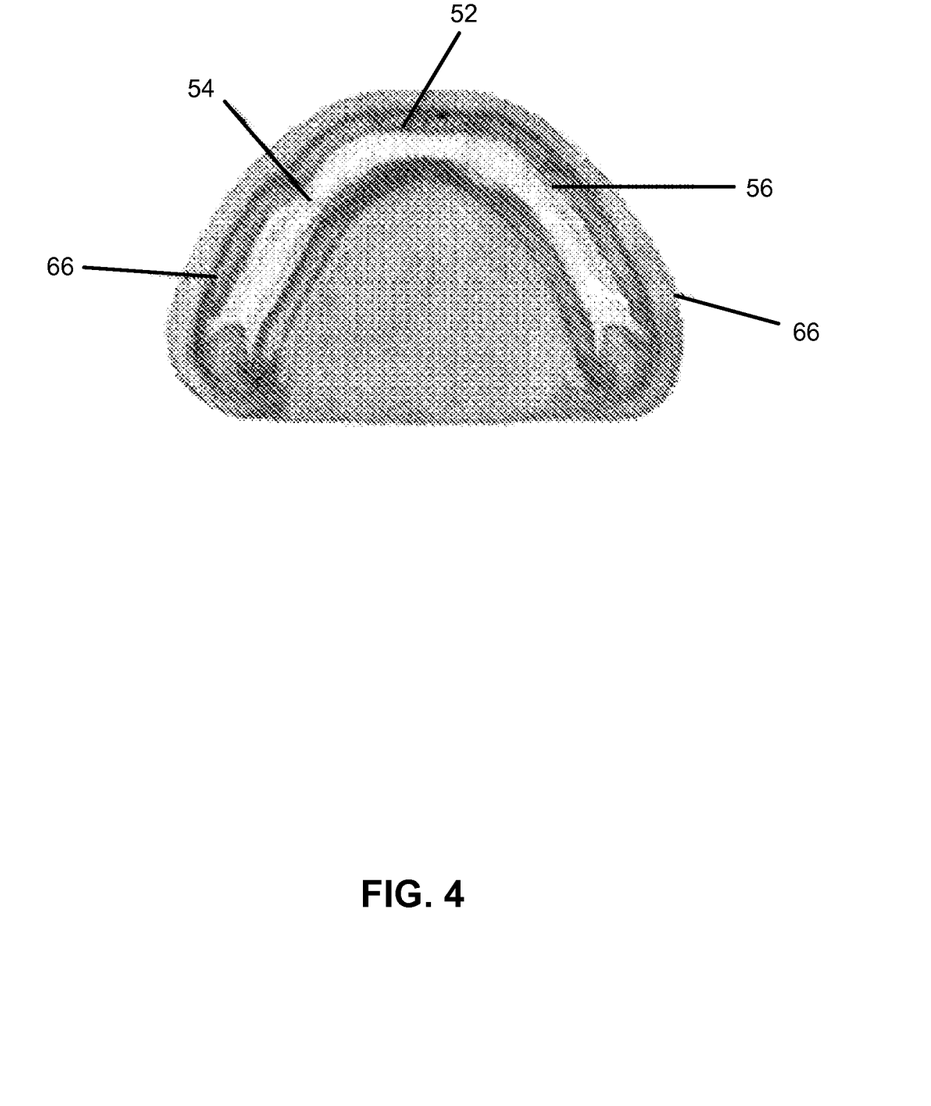
FIG. 4 is an illustration of the mandibular arch.

The system of a preferred embodiment further includes the capability to uniquely distinguish certain anatomical landmarks of the patient from this digital model. These landmarks are used to create features that are registered to ensure their incorporation into the digital model of a denture base from which a denture base is fabricated. The anatomical landmarks of the mandibular arch, as shown in FIG. 4 and of the maxillary arch as shown in FIG. 5 are critical for the proper fit of the denture.

Figure 5:
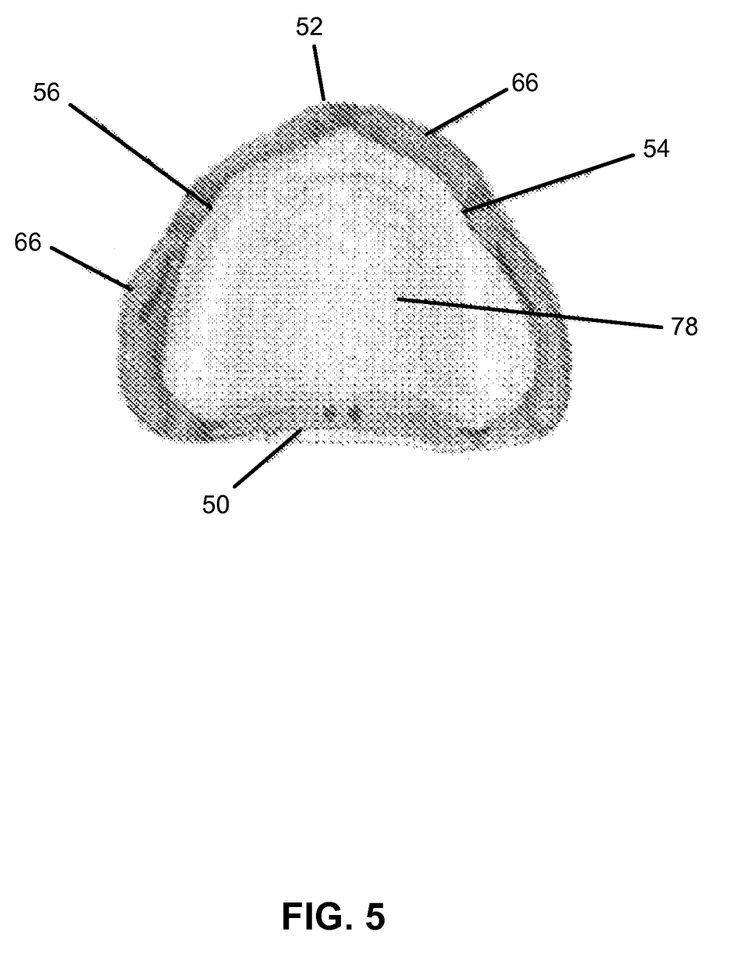
FIG. 5 is an illustration of the maxillary arch.
Figure 6:
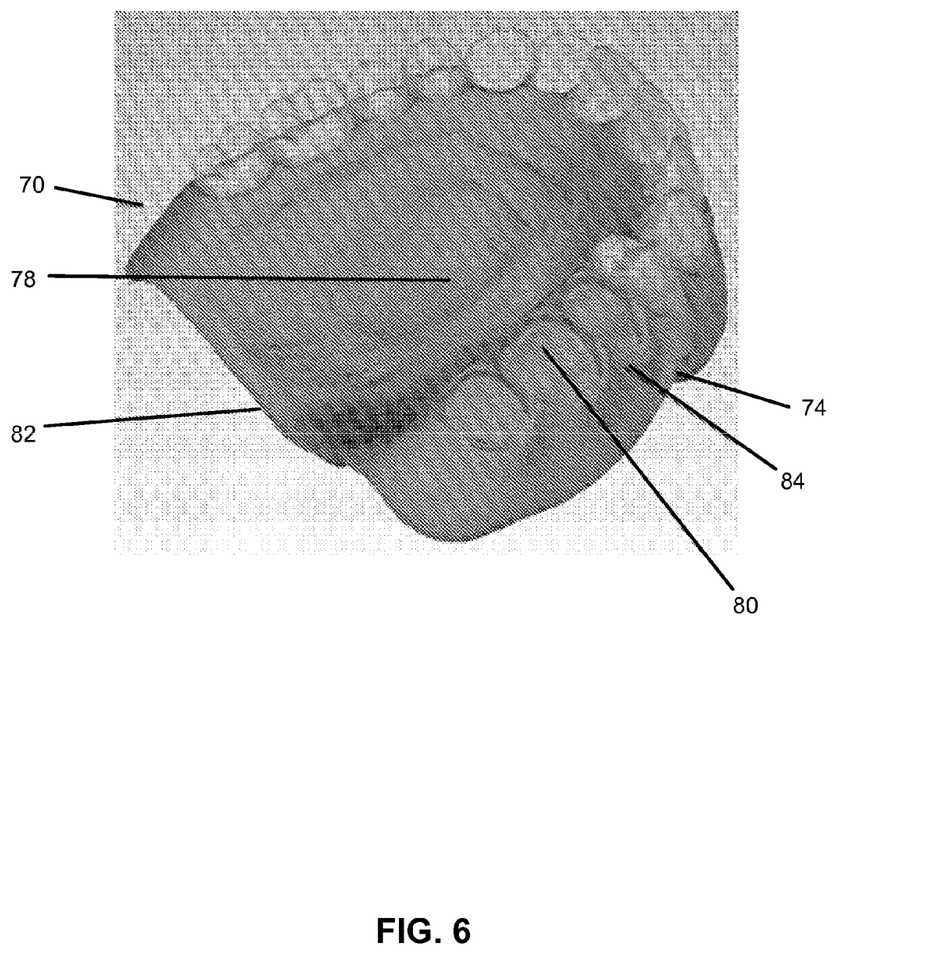
FIG. 6 is an illustration of a rear perspective view of a denture base of a preferred embodiment of the present invention.

One anatomical landmark that is determined preferably by the system, but alternatively by a technician using the system is the line 50 as shown in FIG. 5 between the hard and soft palates. This line is irregular and difficult to determine precisely using current techniques. This line can be determined from the digital model based on the pressure or density in which the bite impressions are formed. For example, the impression will have a greater density at the hard palate due to the greater pressure applied upon it compared to the pressure exerted by the soft palate when the patient bites down on the impression compound. The line may also be readily noticeable simply due to this change in pressure between the palates on the impression compound. This can show up as different colors on the digital model or simply be registered by the system. Other techniques may be used as well. The system then is able to create the post dam along that line of demarcation. This will ensure a tight seal to create a vacuum between the denture and palate to secure the denture.

Figure 7:
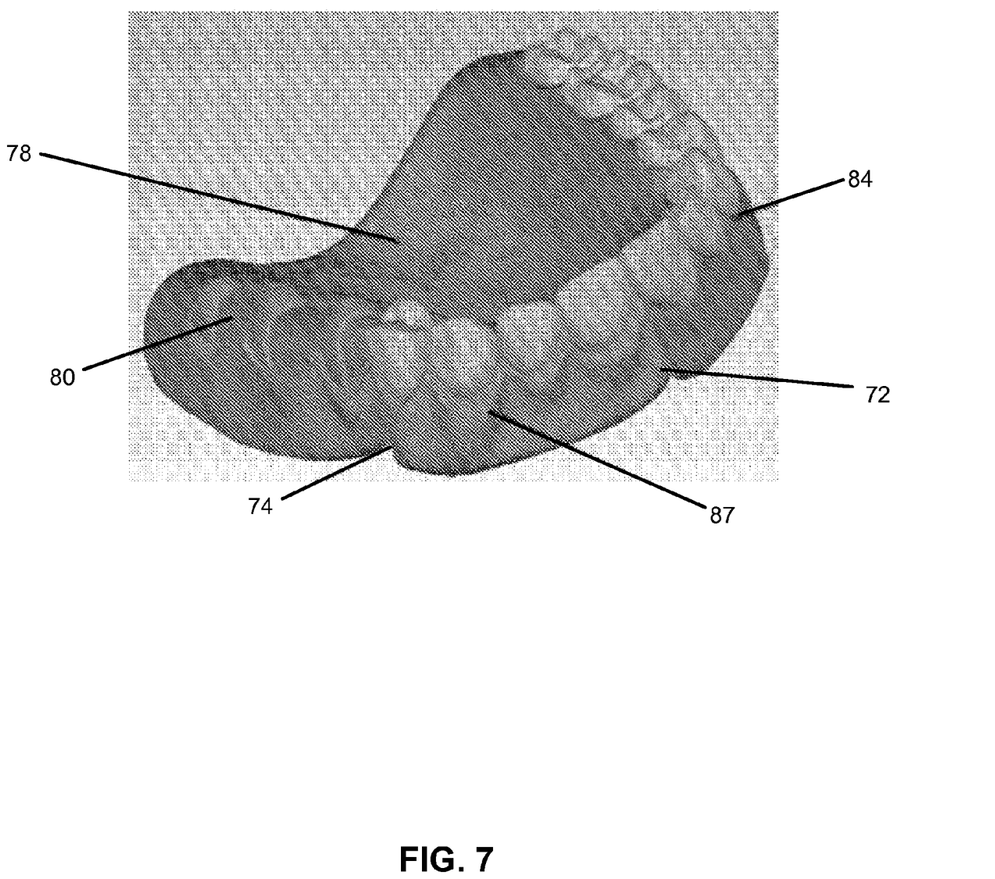
FIG. 7 is a front perspective view of the denture base.
Figure 8:
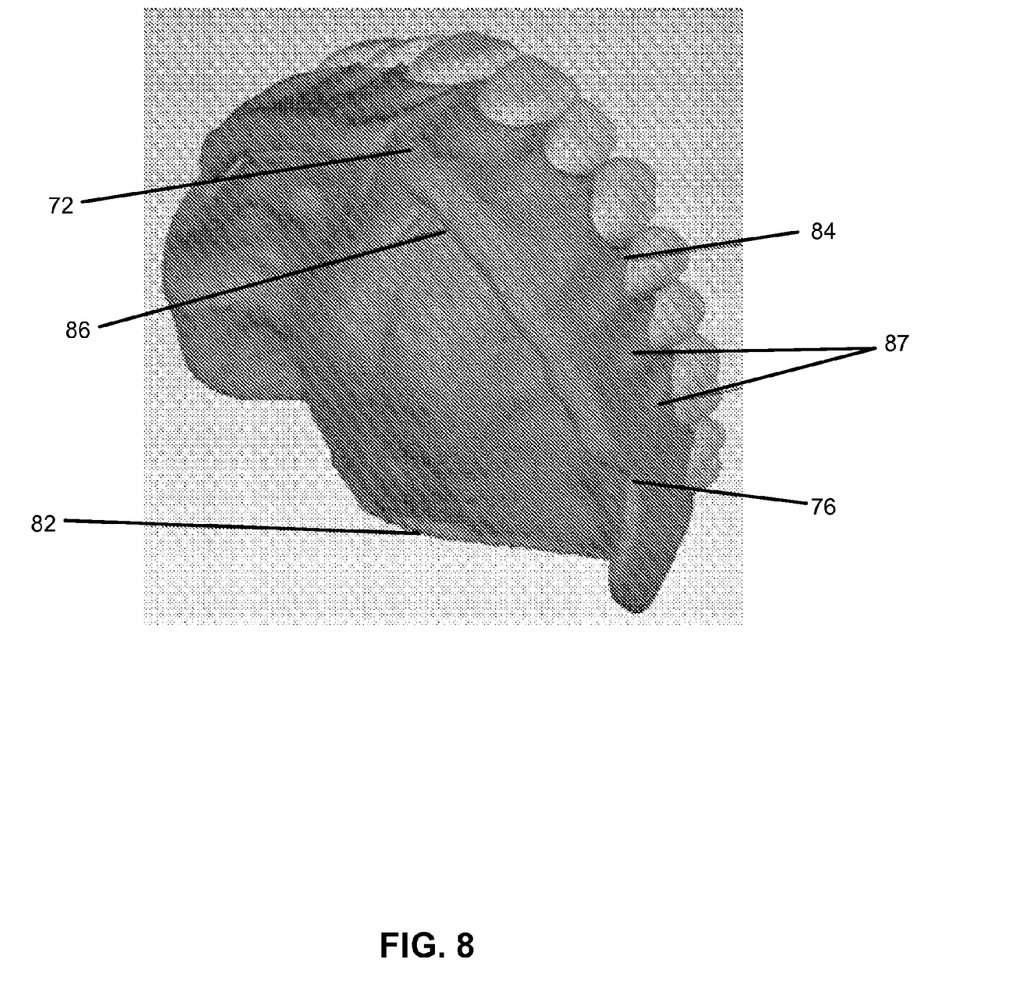
FIG. 8 is top perspective view of the denture base.
Figure 9:
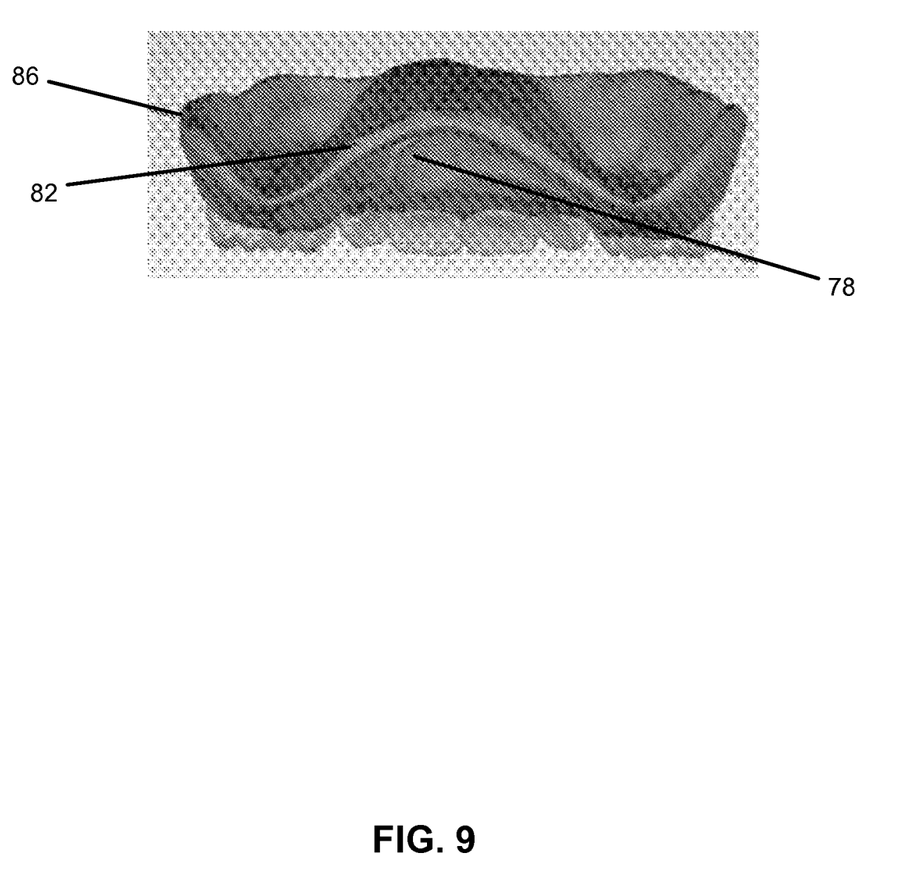
FIG. 9 is a rear view of the denture base.

Another anatomical landmark that is determined is the labial frenum 52. The precise location of the labial frenum can be registered for the creation of the notch 72 in the denture base as shown in FIG. 7. The buccal frenums 54, 56 are also located and registered to create notches 74, 76 in the denture base for these frenums as well. This minimizes dislocation of the denture during speech and improves the comfort, fit and aesthetics of the denture.

The buccal reflection 66 of the patient can be located as well by changes in density due to changes in pressure on the impression compound or simply by the change in structure of the impression. From this precise location of the buccal reflection, the buccal roll 59 can be formed on the denture base. Then, an undercut can be formed in the denture base on the buccal roll. The tissue and muscles surrounding the buccal roll will engage into the undercut to form a gripping region to further secure the denture.

The margin, or trim line along the buccal reflection 66, as shown in FIG. 4 can be precisely located. This reduces the time for technician to carve or trim the denture base after molding and improves the comfort. This margin line can also be registered by the system to be included into the digital denture base and denture base.

The soft tissue lines are also determined from the digital model so that they can be registered and included into the denture base for fabricating the base. In particular, the gingival margin where the gum ends on the teeth and the soft tissue surrounding the roots of the teeth below the gum are mimicked on the denture base. These soft tissue lines are largely for aesthetic reasons but also may improve the comfort to the patient.

The rugae 78 of the individual patient can also be uniquely copied for use in the denture base. Each rugae is unique to an individual and affect the speech and comfort of the individual. The rugae is also used to identify individuals for forensic purposes. The rugae is copied on the tissue side and mimicked on the teeth side. The rugae can also be accentuated or diminished as needed to improve the speech or comfort of the patient. The rugae is registered by the system for copying into the digital denture base.

Figure 11:
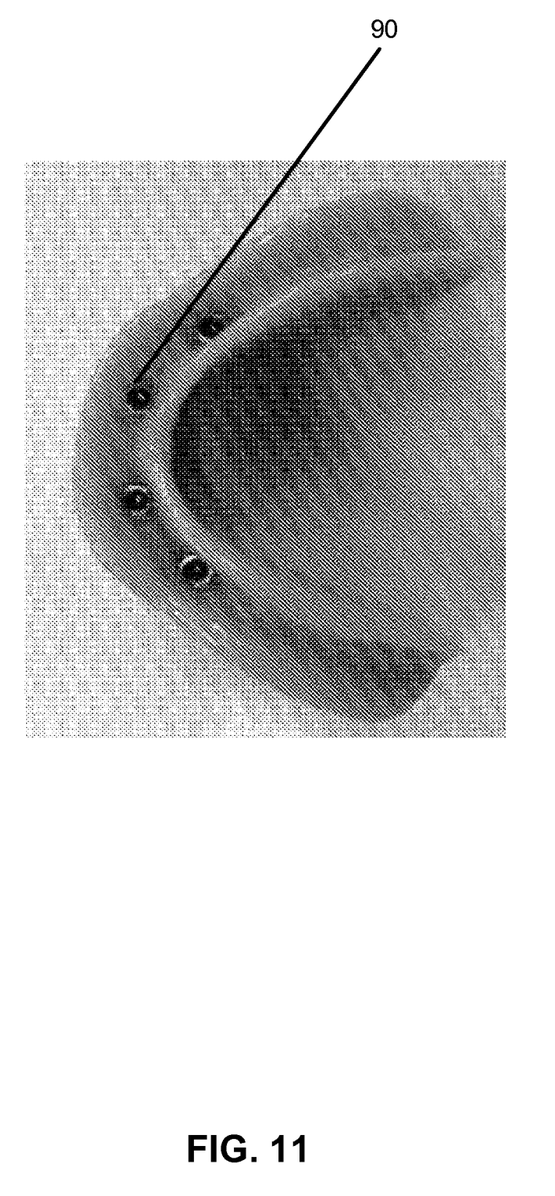
FIG. 11 is an illustration of a denture base with implant housings.

The digital denture model can also be used to identify locations on the optimal denture base for implant supports to be inserted. These supports can be housings such as housings 90 shown in FIG. 11 or bars or other types of supports.

The digital denture model can also be used to identify areas on the denture base which can be thinned to increase comfort while not compromising the structural integrity of the denture base. This can be in the arch, the palatial region and around the teeth pockets. A finite element analysis can also be used to determine these areas.

Other features can be identified and registered by the system if desired. In one embodiment, denture teeth are selected from a library that best fits the digital denture base and modified if necessary. In an alternative embodiment, the denture teeth are fabricated directly from information based on the digital denture base model.

Figure 10:
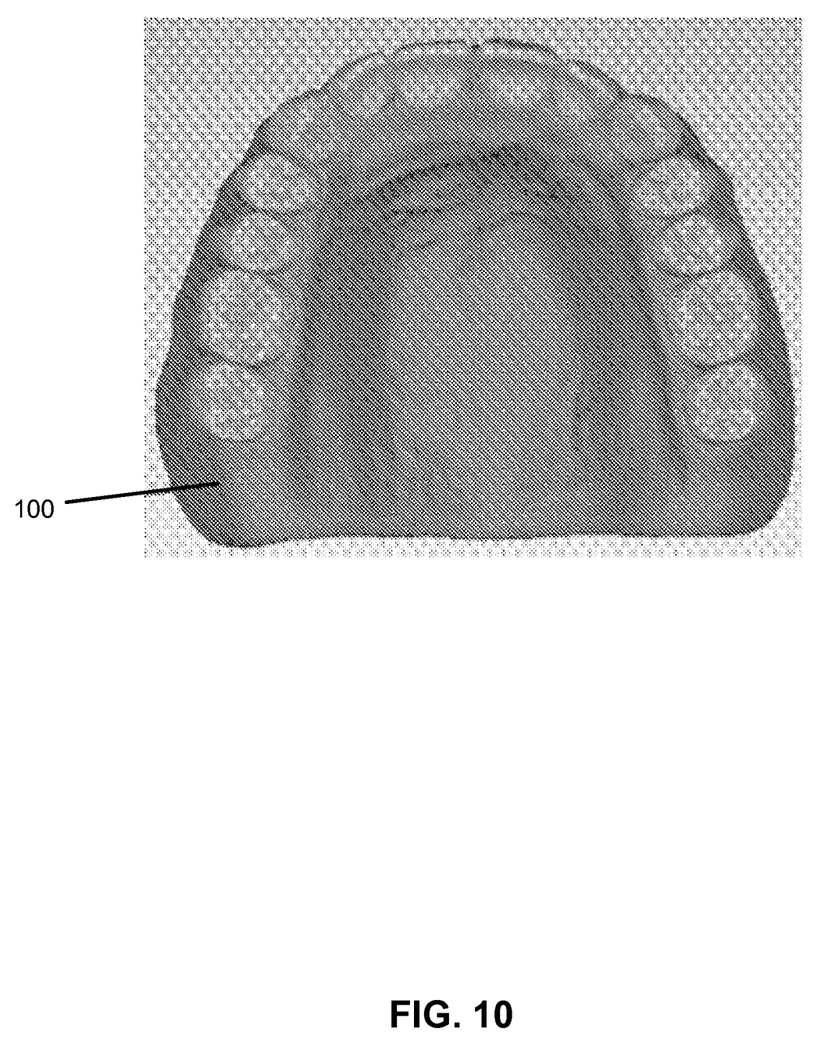
FIG. 10 is a top view of the lower denture base.

Examples of a denture base with the features formed therein are illustrated in FIGS. 6-11. Denture base 70 includes a notch 72 for the labial frenum as well as notches 74, 76 for the buccal frenum. A true rugae 78 that mirrors the patient's rugae is formed as well. Pockets 80 are formed, preferably by milling or rapid prototyping, for the installation of the teeth. The geometry of these pockets has been critically designed for the best occlusal fit of the teeth. Post dam 82 has been formed precisely along the line of between the hard and soft palate. The margins or gum lines 84 and root structures 87 have also been created as well. Critical areas have also been selected to thin the denture base, particularly along the arch palate and teeth pockets. An buccal roll 86 in FIG. 8 may also be formed for engagement along the buccal reflection 66 as well. A lower denture 100 is also shown in FIG. 10.

The denture base is selected or fabricated and the teeth are temporarily installed. This try-in denture is then shipped to the dentist for a patient try-in. If the fit is not satisfactory, then the denture is used as a secondary impression tray and a new impression is created and scanned. This scan along with any additional changes in measurement data is put back into the system. A new denture base is created. The teeth are once again temporarily installed and the denture is ready for another try-in with the patient.

This process is continued until the patient and dentist are satisfied with the denture. Once the denture has been deemed satisfactory, the denture is shipped back to the lab so that the teeth can be permanently installed and the final finish and polish procedures are performed. The finished denture is then shipped to the dentist for the patient final try-in and acceptance.

The system of a preferred embodiment of the present invention can be implemented in many forms. The above description below is simply one example of an implementation of the system.

It is to be expressly understood that the above description is intended only for explanatory purposes and is not meant to limit the scope of the claimed inventions. Other embodiments are considered to be within the scope of the claimed inventions.

What is claimed is:

1. A computer-implemented method for creating anatomical features in a denture, the method comprising:
   creating a digital three dimensional model of the mouth and jaw structure of a patient;
   identifying anatomical landmarks of the patient on the digital model of the mouth and jaw structure of the patient comprising at least a rugae of a soft tissue of the patient;
   creating a digital model of a denture base that includes the identified anatomical landmarks,
   wherein the creating a digital model of a denture base comprises:
      copying the rugae of the soft tissue on the tissue side of the denture base and mimicking the rugae on the teeth side of the denture base to create a true rugae; and
      at least one of accentuating or diminishing the true rugae to improve the speech and comfort of the patient; and
   fabricating a denture base that corresponds to the digital model of the denture base.

2. The method of claim 1 wherein said step of identifying the anatomical landmarks include:
   identifying a line between the hard and soft palates; and
   the step of creating the digital model of the denture base that includes the identified anatomical landmarks includes creating a post dam on the denture base model.

3. The method of claim 1 wherein said step of identifying the anatomical landmarks include:
   identifying a labial frenum; and
   the step of creating the digital model of the denture base that includes the identified anatomical landmarks includes creating a notch based on the labial frenum.

4. The method of claim 1 wherein said step of identifying the anatomical landmarks include:
   identifying buccal frenums; and
   the step of creating the digital model of the denture base that includes the identified anatomical landmarks includes creating notches based on the buccal frenums.

5. The method of claim 1 wherein said step of identifying the anatomical landmarks include:
   identifying a buccal reflection; and
   the step of creating the digital model of the denture base that includes the identified anatomical landmarks includes creating an undercut adjacent a buccal roll corresponding to the buccal reflection.

6. The method of claim 1 wherein said step of identifying the anatomical landmarks include:
   identifying a trim line; and
   the step of creating the digital model of the denture base that includes the identified anatomical landmarks includes creating a margin or trim line along a buccal reflection.

7. The method of claim 1 wherein said step of identifying the anatomical landmarks include:
   identifying areas for thinning on the digital model of the denture base; and
   the step of creating the digital model of the denture base that includes the identified anatomical landmarks includes selectively thinning the denture base on the digital model of the denture base.

8. The method of claim 1 wherein said step of identifying the anatomical landmarks include:
   identifying areas of soft tissue around the teeth of the digital model of the mouth and jaw structure of the patient; and
   the step of creating the digital model of the denture base that includes the identified anatomical landmarks includes creating soft tissue lines around the gum line around the teeth that simulates the root of the tooth.

9. The method of claim 1 wherein said step of identifying the anatomical landmarks include:
   identifying areas for placement of implant supports on the digital model of the mouth and jaw structure of the patient; and
   the step of creating the digital model of the denture base that includes the identified anatomical landmarks includes locations for implant-supports on the digital model of the denture base.

10. A computer-implemented method for creating anatomical features in a denture, the method comprising:
    creating a digital three dimensional model of the mouth and jaw structure of a patient;
    identifying anatomical landmarks of the patient on the digital model of the mouth and jaw structure of the patient comprising at least:
    a rugae of a soft tissue of the patient; and
    areas for thinning on the digital model; and
    creating a digital model of a denture base that includes the identified anatomical landmarks' the step of creating a digital model of a denture base including selectively thinning the denture base on the digital model; and
    fabricating a denture base that corresponds to the digital model of the denture base.

11. The method of claim 10 wherein the creating further comprises:
    copying the rugae of the soft tissue on the tissue side of the denture base and mimicking the rugae on the teeth side of the denture base to create a true rugae; and
    at least one of accentuating or diminishing the true rugae to improve the speech and comfort of the patient.

12. The method of claim 10 wherein said step of identifying the anatomical landmarks include:
    identifying a line between the hard and soft palates; and
    the step of creating the digital model of the denture base that includes the identified anatomical landmarks includes creating a post dam on the denture base model.

13. The method of claim 10 wherein said step of identifying the anatomical landmarks include:
    identifying a labial frenum; and
    the step of creating the digital model of the denture base that includes the identified anatomical landmarks includes creating a notch based on the labial frenum.

14. The method of claim 10 wherein said step of identifying the anatomical landmarks include:
    identifying buccal frenums; and
    the step of creating the digital model of the denture base that includes the identified anatomical landmarks includes creating notches based on the buccal frenums.

15. The method of claim 10 wherein said step of identifying the anatomical landmarks include:
    identifying a buccal reflection; and
    the step of creating the digital model of the denture base that includes the identified anatomical landmarks includes creating an undercut adjacent a buccal roll corresponding to the buccal reflection.

16. The method of claim 10 wherein said step of identifying the anatomical landmarks include:
    identifying a trim line; and
    the step of creating the digital model of the denture base that includes the identified anatomical landmarks includes creating a margin or trim line along a buccal reflection.

17. The method of claim 10 wherein said step of identifying the anatomical landmarks include:
    identifying areas of soft tissue around the teeth of the digital model of the mouth and jaw structure of the patient; and
    the step of creating the digital model of the denture base that includes the identified anatomical landmarks includes creating soft tissue lines around the gum line around the teeth that simulates the root of the tooth.

18. The method of claim 10 wherein said step of identifying the anatomical landmarks include:
    identifying areas for placement of implant supports on the digital model of the mouth and jaw structure of the patient; and
    the step of creating the digital model of the denture base that includes the identified anatomical landmarks includes locations for implant-supports on the digital model of the denture base.

* * * * *